(12) United States Patent
Vendrely et al.

(10) Patent No.: US 7,935,118 B2
(45) Date of Patent: May 3, 2011

(54) PROSTHESIS REMOVAL CUTTING GUIDE, CUTTING TOOL AND METHOD

(75) Inventors: Tim Vendrely, Warsaw, IN (US); M. Kathleen Willison, Indian River, MI (US); Lowry Barnes, Little Rock, AR (US)

(73) Assignee: DePuy Products, Inc., Warsaw, IN (US)

(*) Notice: Subject to any disclaimer, the term of this patent is extended or adjusted under 35 U.S.C. 154(b) by 1219 days.

(21) Appl. No.: 10/176,934

(22) Filed: Jun. 21, 2002

(65) Prior Publication Data
US 2003/0236525 A1    Dec. 25, 2003

(51) Int. Cl.
*A61F 5/00* (2006.01)
(52) U.S. Cl. .......................... 606/87; 606/99
(58) Field of Classification Search .............. 606/79–82, 606/84–89, 96–100, 104
See application file for complete search history.

(56) References Cited

U.S. PATENT DOCUMENTS

| | | | |
|---|---|---|---|
| 1,630,239 A | | 5/1927 | Binkley et al. |
| 3,820,167 A | | 6/1974 | Sivash |
| 3,835,858 A | * | 9/1974 | Hagen ........................ 606/180 |
| 3,839,742 A | | 10/1974 | Link |
| 3,855,638 A | | 12/1974 | Pilliar |
| 3,867,932 A | | 2/1975 | Huene |
| 3,872,519 A | | 3/1975 | Giannestras et al. |
| 3,886,599 A | | 6/1975 | Schlein |
| 3,889,300 A | | 6/1975 | Smith |
| 3,896,502 A | | 7/1975 | Lennox |
| 3,943,576 A | | 3/1976 | Sivash |
| 3,975,778 A | | 8/1976 | Newton, III |
| 3,987,500 A | | 10/1976 | Schlein |
| 3,996,625 A | | 12/1976 | Noiles |
| 4,021,864 A | | 5/1977 | Waugh |
| 4,069,518 A | | 1/1978 | Groth, Jr. et al. |
| 4,077,070 A | | 3/1978 | Sivash |
| 4,232,404 A | | 11/1980 | Samuelson et al. |
| 4,421,112 A | | 12/1983 | Mains et al. |
| 4,450,591 A | | 5/1984 | Rappaport |
| 4,467,801 A | | 8/1984 | Whiteside |
| 4,470,158 A | | 9/1984 | Pappas et al. |
| 4,474,177 A | | 10/1984 | Whiteside |
| 4,524,766 A | | 6/1985 | Petersen |
| 4,530,114 A | | 7/1985 | Tepic |

(Continued)

FOREIGN PATENT DOCUMENTS

DE    2830354 A1    2/1979

(Continued)

OTHER PUBLICATIONS

S-ROM Total Hip System Surgical Technique Brochure (0601-36-050 (Rev. 1)—DePuy Orthopaedics, Inc. & DePuy International, Ltd., published in the USA and Leeds England, 2002.
S-ROM Total Hip System Product Codes & Surgical Technique Brochure—DePuy Orthopaedics, Inc., & DePuy International, Ltd., published in the USA and Leeds England, 2002.

(Continued)

*Primary Examiner* — Thomas C Barrett
*Assistant Examiner* — Michael J Araj
(74) *Attorney, Agent, or Firm* — Maginot, Moore & Beck (57) ABSTRACT

A kit for removal of bone adjacent to an implanted prosthesis. The kit includes a guide for cooperation with the prosthesis and a tool constrainable by the guide for removal of the bone. The guide may include a first portion of the guide that is co-operable with the tool and a second portion of the guide that is co-operable with the prosthesis.

11 Claims, 8 Drawing Sheets

U.S. PATENT DOCUMENTS

| | | |
|---|---|---|
| 4,551,863 A | 11/1985 | Murray |
| 4,567,885 A | 2/1986 | Androphy |
| 4,703,751 A | 11/1987 | Pohl |
| 4,708,139 A | 11/1987 | Dunbar, IV |
| 4,719,908 A | 1/1988 | Averill et al. |
| 4,721,104 A | 1/1988 | Kaufman et al. |
| 4,755,185 A | 7/1988 | Tarr |
| 4,784,126 A | 11/1988 | Hourahane |
| 4,790,852 A | 12/1988 | Noiles |
| 4,846,839 A | 7/1989 | Noiles |
| 4,865,603 A | 9/1989 | Noiles |
| 4,885,603 A | 12/1989 | Tomizawa et al. |
| 4,892,093 A | 1/1990 | Zarnowski et al. |
| 4,926,847 A * | 5/1990 | Luckman .................. 606/88 |
| 4,952,213 A | 8/1990 | Bowman et al. |
| 4,952,214 A * | 8/1990 | Comparetto ................ 606/87 |
| 4,968,316 A | 11/1990 | Hergenroeder |
| 5,011,496 A | 4/1991 | Forte et al. |
| 5,035,699 A | 7/1991 | Coates |
| 5,053,037 A | 10/1991 | Lackey |
| 5,122,144 A | 6/1992 | Bert et al. |
| 5,147,364 A * | 9/1992 | Comparetto ................ 606/85 |
| 5,163,940 A | 11/1992 | Bourque |
| 5,167,619 A | 12/1992 | Wuchinich |
| 5,190,547 A | 3/1993 | Barber, Jr. et al. |
| 5,207,712 A | 5/1993 | Cohen |
| 5,234,433 A | 8/1993 | Bert et al. |
| 5,246,444 A | 9/1993 | Schreiber |
| 5,257,995 A * | 11/1993 | Umber et al. .............. 606/99 |
| 5,282,803 A | 2/1994 | Lackey |
| 5,290,291 A * | 3/1994 | Linden ..................... 606/99 |
| 5,295,992 A | 3/1994 | Cameron |
| 5,312,411 A | 5/1994 | Steele et al. |
| 5,312,412 A | 5/1994 | Whipple |
| 5,314,482 A | 5/1994 | Goodfellow et al. |
| 5,326,365 A | 7/1994 | Alvine |
| 5,342,368 A | 8/1994 | Petersen |
| 5,344,423 A | 9/1994 | Dietz et al. |
| 5,360,450 A | 11/1994 | Giannini |
| 5,364,402 A | 11/1994 | Mumme et al. |
| 5,395,376 A | 3/1995 | Caspari et al. |
| 5,403,321 A | 4/1995 | DiMarco |
| 5,409,489 A | 4/1995 | Sioufi |
| 5,449,360 A | 9/1995 | Schreiber |
| 5,454,816 A | 10/1995 | Ashby |
| 5,474,559 A * | 12/1995 | Bertin et al. .............. 606/89 |
| 5,484,437 A | 1/1996 | Michelson |
| 5,484,446 A | 1/1996 | Burke et al. |
| 5,486,180 A * | 1/1996 | Dietz et al. ............... 606/87 |
| 5,489,180 A * | 2/1996 | Ichihara et al. ............. 411/544 |
| 5,496,324 A | 3/1996 | Barnes |
| 5,520,695 A | 5/1996 | Luckman |
| 5,534,005 A | 7/1996 | Tokish, Jr. et al. |
| 5,540,692 A | 7/1996 | Tidwell |
| 5,562,674 A | 10/1996 | Stalcup et al. |
| 5,571,110 A | 11/1996 | Matsen, III et al. |
| 5,584,839 A | 12/1996 | Gieringer |
| 5,593,411 A | 1/1997 | Stalcup et al. |
| 5,601,563 A | 2/1997 | Burke et al. |
| 5,613,970 A | 3/1997 | Houston et al. |
| 5,613,971 A | 3/1997 | Lower et al. |
| 5,624,443 A | 4/1997 | Burke |
| 5,624,444 A | 4/1997 | Wixon et al. |
| 5,634,927 A | 6/1997 | Houston et al. |
| 5,643,272 A | 7/1997 | Haines et al. |
| 5,653,714 A | 8/1997 | Dietz et al. |
| 5,683,397 A * | 11/1997 | Vendrely et al. ............ 606/88 |
| 5,709,689 A * | 1/1998 | Ferrante et al. ........... 606/86 R |
| 5,733,290 A | 3/1998 | McCue et al. |
| 5,743,910 A | 4/1998 | Bays et al. |
| 5,766,259 A | 6/1998 | Sammarco |
| 5,769,854 A | 6/1998 | Bastian et al. |
| 5,810,827 A | 9/1998 | Haines et al. |
| 5,879,354 A | 3/1999 | Haines et al. |
| 5,902,340 A * | 5/1999 | White et al. ............... 128/898 |
| 5,916,220 A | 6/1999 | Masini |
| 5,925,049 A | 7/1999 | Gustilo et al. |
| 5,938,665 A | 8/1999 | Martin |
| 6,056,754 A | 5/2000 | Haines et al. |
| 6,090,114 A | 7/2000 | Matsuno et al. |
| 6,106,529 A | 8/2000 | Techiera |
| 6,139,551 A | 10/2000 | Michelson |
| 6,179,877 B1 | 1/2001 | Burke |
| 6,183,519 B1 | 2/2001 | Bonnin et al. |
| 6,187,012 B1 * | 2/2001 | Masini ..................... 606/99 |
| 6,193,723 B1 | 2/2001 | Cripe et al. |
| 6,197,029 B1 | 3/2001 | Fujimori et al. |
| 6,197,064 B1 | 3/2001 | Haines et al. |
| 6,277,121 B1 | 8/2001 | Burkinshaw et al. |
| 6,322,564 B1 * | 11/2001 | Surma ..................... 606/79 |
| 6,342,057 B1 | 1/2002 | Brace et al. |
| 6,355,045 B1 | 3/2002 | Gundlapalli et al. |
| 6,361,506 B1 | 3/2002 | Saenger et al. |
| 6,409,767 B1 | 6/2002 | Perice et al. |
| 6,482,209 B1 | 11/2002 | Engh et al. |
| 6,488,687 B1 | 12/2002 | Masini |
| 6,520,964 B2 | 2/2003 | Tallarida et al. |
| 6,537,280 B2 * | 3/2003 | Dinger et al. ............. 606/85 |
| D473,307 S | 4/2003 | Cooke |
| 6,554,837 B1 | 4/2003 | Hauri et al. |
| 6,554,838 B2 | 4/2003 | McGovern et al. |
| 6,575,980 B1 * | 6/2003 | Robie et al. .............. 606/88 |
| 6,663,669 B1 | 12/2003 | Reiley |
| 6,852,130 B2 | 2/2005 | Keller et al. |
| 6,863,691 B2 | 3/2005 | Short et al. |
| 6,926,739 B1 | 8/2005 | O'Connor et al. |
| 7,011,664 B2 * | 3/2006 | Haney et al. .............. 606/87 |
| 7,033,362 B2 | 4/2006 | McGahan et al. |
| 7,090,677 B2 * | 8/2006 | Fallin et al. .............. 606/80 |
| 7,240,588 B1 * | 7/2007 | Rinner ..................... 76/119 |
| 2002/0055744 A1 | 5/2002 | Reiley |
| 2002/0183760 A1 | 12/2002 | McGovern et al. |
| 2004/0002768 A1 | 1/2004 | Parks et al. |
| 2004/0030399 A1 | 2/2004 | Asencio |
| 2004/0122523 A1 | 6/2004 | Guzman |
| 2004/0133282 A1 | 7/2004 | Deffenbaugh et al. |
| 2004/0162619 A1 * | 8/2004 | Blaylock et al. ........... 623/20.16 |
| 2004/0167631 A1 | 8/2004 | Luchesi et al. |
| 2004/0186585 A1 | 9/2004 | Feiwell |
| 2005/0288792 A1 | 12/2005 | Landes et al. |
| 2006/0142870 A1 | 6/2006 | Robinson et al. |

FOREIGN PATENT DOCUMENTS

| | | |
|---|---|---|
| DE | 19501550 A1 | 7/1996 |
| EP | 0327249 A2 | 8/1989 |
| EP | 0682916 B1 | 11/1995 |
| EP | 0800803 B1 | 10/1997 |
| EP | 0864304 B1 | 9/1998 |
| EP | 0864305 B1 | 9/1998 |
| EP | 0 962 190 A2 | 12/1999 |
| FR | 2220235 A1 | 10/1974 |
| FR | 2543821 A3 | 10/1984 |
| FR | 2615726 A1 | 12/1988 |
| FR | 2616059 A1 | 12/1988 |
| FR | 2676917 A1 | 12/1992 |
| FR | 2680968 A1 | 3/1993 |
| FR | 2684291 A1 | 6/1993 |
| FR | 2700462 A1 | 7/1994 |
| FR | 2730157 A1 | 8/1996 |
| FR | 2759900 A1 | 8/1998 |
| FR | 2808994 A1 | 1/2001 |
| WO | 9107931 A1 | 6/1991 |
| WO | 9405211 A1 | 3/1994 |
| WO | 0067650 A1 | 11/2000 |
| WO | WO 03/034955 A1 | 5/2003 |
| WO | 2005030098 A1 | 4/2005 |
| WO | 2005041823 A1 | 5/2005 |

OTHER PUBLICATIONS

Wright Medical Technology, Advance Unicompartmental Knee System. Surgical Technique, (12 pages).

Stryker Howmedical Osteonics, The Minimally Invasive Uni Knee System, Surgical Technique, 2002 (20 pages).

\* cited by examiner

PROSTHESIS REMOVAL CUTTING GUIDE, CUTTING TOOL AND METHOD

CROSS-REFERENCE TO RELATED APPLICATIONS

Cross-reference is made to the following applications: DEP 623 entitled "PROSTHESIS CAVITY CUTTING GUIDE, CUTTING TOOL AND METHOD" and DEP 704 entitled "PROSTHESIS CUTTING GUIDE, CUTTING TOOL AND METHOD" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Joint replacement surgery is quite common and it enables many individuals to function properly when they otherwise would not be possible to do so. Such patients of joint replacement surgery typically suffer from osteoarthritis or rheumatoid arthritis. Artificial joints usually comprise metallic, ceramic and/or plastic components that are fixed to existing bone.

Such joint replacement surgery is otherwise known as total joint arthroplasty. Total joint arthroplasty is a well-known surgical procedure by which a diseased and/or damaged joint is replaced with a prosthetic joint. In a typical total joint arthroplasty, the ends or distal portions of the bone adjacent the joint are resected or a portion of the distal part of the bone is removed and the artificial joint is secured thereto.

For many patients suffering from osteoarthritis or rheumatoid arthritis, the procedure of total joint arthroplasty results in a prosthetic joint, which serves the patient through his or her entire life. Unfortunately, for a variety of reasons, some patients having total joint arthroplasty are not as fortunate, and the prosthetic joint must be replaced. Such a procedure to replace a prosthetic joint with a replacement prosthetic joint is called revision total joint arthroplasty. For such replacement surgery, the original or primary implant must be removed from the body or severed from the bone.

Proper implantation of an implant during total joint arthroplasty frequently suggests that the joint be firmly secured to the adjoining bone. For example, when utilizing bone cement to secure the original prosthetic joint, pressure is applied when utilizing the cement to cause the cement to interdigitate or move somewhat in to the cancellous bone around the joint.

Alternatively, when a prosthetic joint is utilized without bone cement, often the prosthetic joint includes an outer porous coating, which provides over time for bony ingrowth within the porous portion of the prosthesis. Whether the implant is secured with interdigitated cement or bony ingrowth, the removal of the prosthesis from the bone may be quite difficult. Typically, to remove the prosthesis, tools, for example, in the form of hand tools such as Moreland instruments or Dremel type-cutting instruments are used.

These cutting instruments are utilized by the surgeon in a free hand procedure in which the tools are manually moved near the periphery of the prosthesis until the prosthesis and the bone are separated from each other. Since this procedure is done manually and freehand with no additional tools to assist in the placement and movement of the hand tools around the bone, the result is often that excess bone is removed from the implant. Generally, good surgical procedure requires and suggests that only the minimal amount of bone be removed from the patient. Furthermore, to implant replacement prosthesis, bone must remain to secure the replacement prosthesis to the bone.

A need does exist for improved method and instrumentation to assist in the removal of a joint implant which provides for more accurate placement of the tools during the cutting procedure, and that provides for a procedure that also may be less time consuming than the current manual freehand approach.

SUMMARY OF THE INVENTION

The present invention is directed to a revision cutting guide and method, which is utilized with a cutting tool to create a precise resection of bone adjacent to the existing prosthesis. The cutting guide provides for an accurate cut both in the outlined shape and the proximity of the cut to the current implant. The tool is so guided such that the cuts are quite accurate and may be made quite rapidly. Therefore, a minimum amount of material is removed and the time to perform the revision surgery is minimized.

According to one embodiment of the present invention, a kit is provided for removal of bone adjacent to an implanted prosthesis. The kit includes a guide for cooperation with the prosthesis and a tool. The tool is constrainable by the guide for removal of the bone.

According to another embodiment of the present invention, a guide is provided for guiding a tool for use in removal of bone adjacent to a prosthesis. The guide includes a first portion thereof cooperable with the tool and a second portion. The second portion is co-operable with the prosthesis.

According to yet another embodiment of the present invention, a tool adapted for use with a guide for removal of bone adjacent to an implanted prosthesis is provided. The tool is constrainable by the guide for removal of the bone.

According to a further embodiment of the present invention, there is provided a method for removing an implanted prosthesis to prepare a patient for total joint revision arthroplasty. The method includes the steps of providing a guide defining an opening therein, placing the guide in cooperation with the prosthesis, providing a tool adapted for cooperation with the opening, inserting the tool at least partially within the opening, causing the tool to move relatively to the prosthesis, advancing the tool within the opening at least partially around the periphery of the prosthesis, and extracting the prosthesis from the patient.

The technical advantages of the present invention include a more accurate imprint or location of the cuts around the implanted prosthesis stem to be removed. For example, according to one aspect of the present invention, the guide includes channels positioned about the outer periphery of the guide, which conform to a path slightly outside of the outer periphery of the implant to be removed. The tool is moved about the pocket to provide for cuts outside the prosthesis that are very close to the prosthesis, well defined and accurate. Thus, the present invention provides for improved accuracy cuts and minimal removal of bone when making cuts to loosen the prosthesis for its removal.

Another technical advantage of the present invention reduces damage to the tool caused by the tool being in contact in cutting the hardened prosthesis. For example, according to one aspect of the present invention the tool includes channels, which guide the tool in a spaced apart relationship to the prosthesis.

Further, according to a another aspect of the present invention, the guide includes a first guide feature which cooperates with a prosthesis feature such that the guide and the prosthesis are aligned such that the movement of the tool along the channels provides for an accurate space from the prosthesis cut such that the tool does not contact the prosthesis and cause damage to the tool.

A further technical advantage of the present invention includes reduced damage and minimal removal of bone during the removal cuts performed by the tool. For example, according to one aspect of the present invention, the guide includes channels which may be aligned with the periphery of the tool and the guide, has a feature which may be aligned with a feature on the prosthesis such that if the tool is moved about the channels of the guide the cutting tool accurately cuts a minimal path adjacent to the prosthesis such that the amount of bone loss during prosthesis removal is minimized.

The technical advantages of the present invention further include the ability to form the removal cuts to remove the implant in a much greater speed. For example, according to one aspect of the present invention, the guide includes a plurality of spaced-apart channels which occupy most of the cross sectional area of the guide such that when the guide, in cooperation with the tool, is used to form the pockets for the implant, only a quick and simple use of an osteotome to remove the small portions of the material remaining after the utilization of the tool and the guide can be quickly accomplished. Therefore, with the rapid use of the guide and the tool, as well as, a minimal use of the osteotome, the pocket may be prepared very quickly and accurately.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings. According to the present invention and referring now to FIG. 1, a kit 10 is shown. The kit 10 is utilized for removal of bone 12 adjacent to an implanted prosthesis 14. The kit 10 includes a guide 16 for cooperation with the prosthesis 14 and a tool 20. The tool 20 is constrainable by the guide 16 for removal of the bone 12. The guide 16 may include a first portion 21 of the guide 16, which is co-operable with the tool 20. The guide 16 may further include a second portion 24, which is co-operable with the prosthesis 14.

Figure 1:
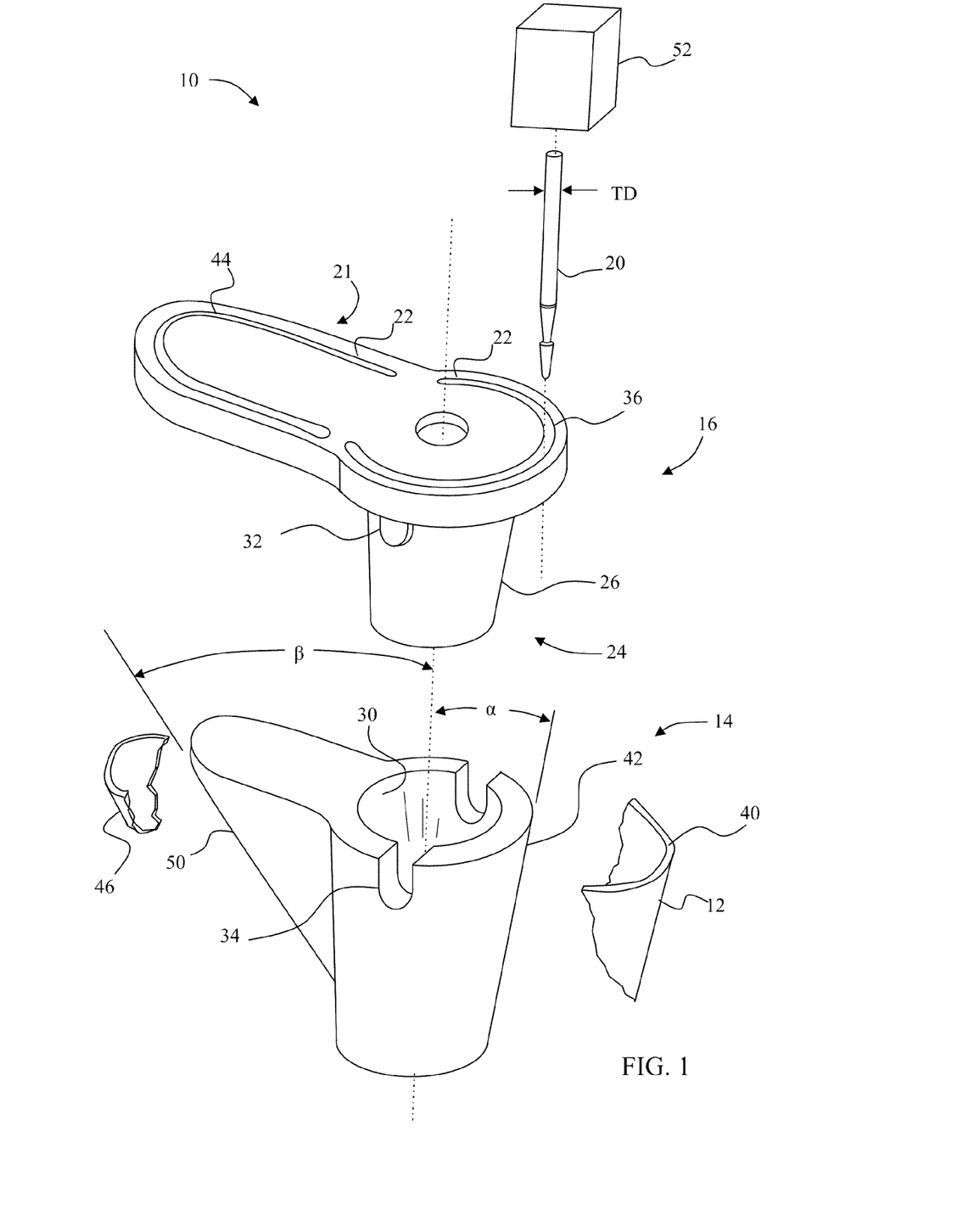
FIG. 1 is an exploded perspective view of a kit according to the present invention, including a guide and tool is shown in cooperation with a femoral component of a hip prosthesis in accordance with an embodiment of the present invention.

It should be appreciated that the first portion, 21 of the guide 16 may have any shape suitable to provide for the guiding of the tool; for example, the first portion 21 may be in the form of a channel. The tool 20 may be guided within the channel 22.

The second portion 24 of the guide 16 may have any shape or configuration capable of cooperating with the prosthesis 14. For example, the second portion 24 of the guide 16 may include an external taper 26 co-operable with an internal taper 30 on the prosthesis 14.

While the channel 22 may have any suitable shape, preferably, the channel 22 has a shape so that it may guide the tool 20 in a path adjacent and slightly spaced from the prosthesis 14. For example, if the prosthesis 14 has a generally arcuate periphery, the channel 22 will correspondingly, preferably, have a generally arcuate shape.

Preferably, and as shown in FIG. 1, the guide 16 will include a guide orientation feature 32 which, is used to angularly orient the guide 16 with respect to the prosthesis 14. The guide orientation feature 32 may cooperate, for example, with a prosthesis orientation feature 34 located on the prosthesis 14.

While it should be appreciated that the present invention may be practiced with a solitary channel 22, as shown in FIG. 1, the first portion 21 may include a first channel 36 which is adapted for cooperation with the tool 20 for removal of a first portion 40 of the bone 12 adjacent a first portion 42 of the prosthesis 14.

The guide 16 may further include a second channel 44 adapted for cooperation with the tool 20 for removal of a second portion 46 of the bone 12 at a location adjacent a second portion 50 of the prosthesis 14.

While it should be appreciated that the tool 20 may be a hand tool that is manipulated by the surgeon, the kit 10, as shown in FIG. 1, may further include a power source 52 to move the tool 20 with respect to the prosthesis 14 so that the tool 20 may be utilized to remove the portions 40 and 46 of the long bone 12. The power source 52 may be any electrical, pneumatic or hydraulic power source capable of reciprocating, rotating or other motion causing the tool 20 to move. Preferably, the power source 52 is compatible with an operating room environment and has a capability of being sterilized or capability of avoiding contamination to the operating room.

A purpose of the guide of the present invention is to guide or position the tool with respect to the implanted prosthesis, which is to be removed. Preferably, the guide is designed such that the tool is caused to move in a path parallel to and very slightly spaced from the outer periphery of the prosthesis. The shape of the prosthesis may very widely depending on the size of the patient, the particular anatomical joint, and the manufacturer and type of prosthesis.

Differences in patient anatomy and physical condition, as well as differences in surgical techniques and surgeon preferences, necessitate prostheses having a wide variety of shapes and sizes. Consequently, it may be desirable to have a guide that is customized for a particular size and shape of the prosthesis. Such a guide can be designed to assure that the tool path width is minimized and that the tool is accurately positioned in a minimal apart space relationship from the prosthesis to be removed such that a minimal amount of the patients bone is sacrificed in the removal of the prosthesis.

The guide 16, as shown in FIGS. 1 through 5, is designed to remove the proximal portion of a S-ROM total hip system provided by DePuy Orthopaedics Incorporated. The S-ROM total hip system includes a sleeve which is a separate component from the remainder of the total hip system and which sleeve may be separately removed from the patient during revision total joint arthroplasty. The guide 16, as shown in FIGS. 1 through 4, is particularly well suited for the removal of the sleeve of a DePuy S-ROM total hip system.

Figure 5:
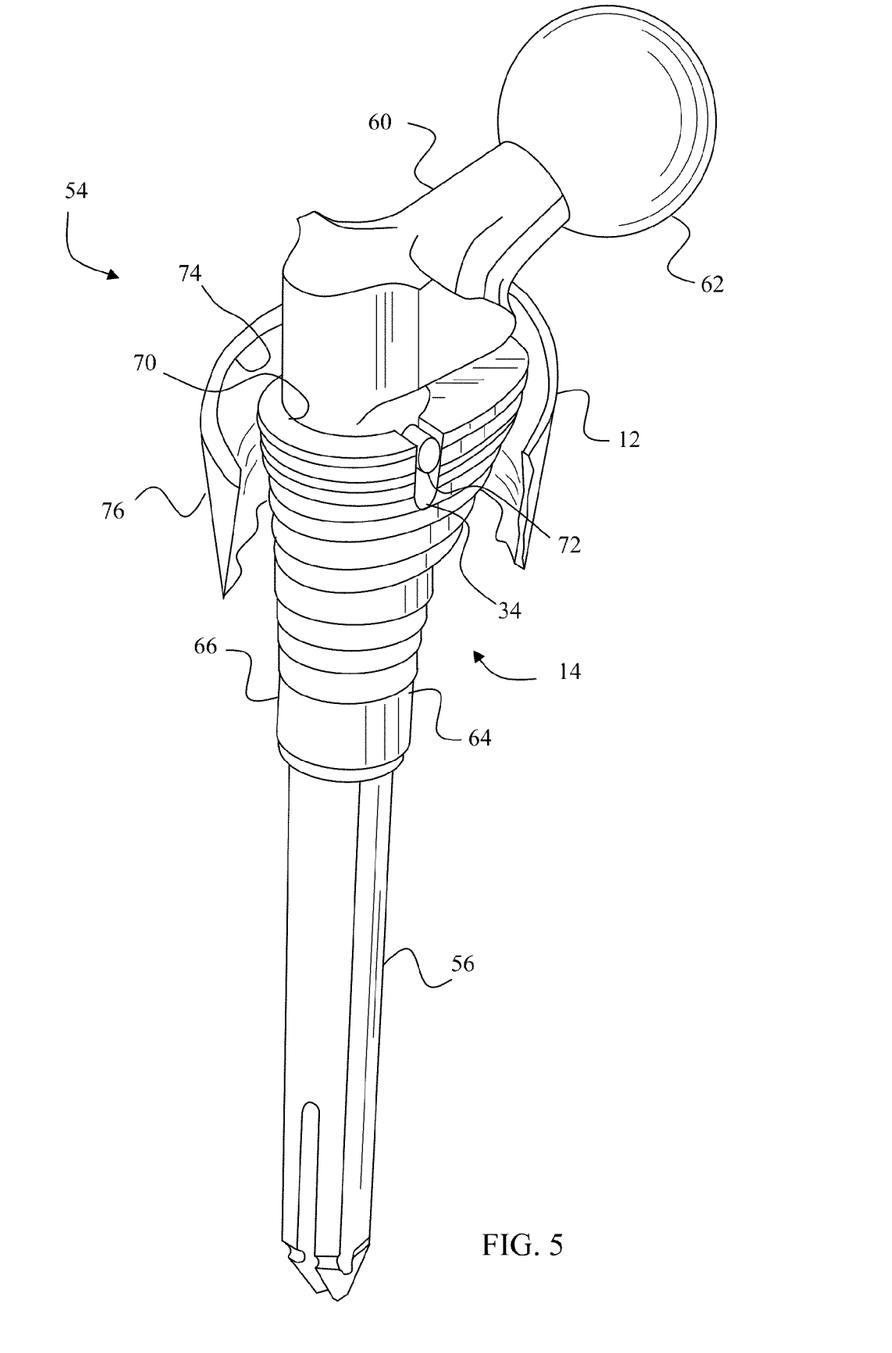
FIG. 5 is a perspective view of a femoral hip stem prosthesis assembly with which the kit of FIG. 1 may be used.

Referring now to FIG. 5, a femur portion or hip stem 54 is shown as a part of an artificial hip joint. The hip stem 54 includes a stem 56, which is attached to arm or neck 60 and ball or head 62. Stem 56, arm 60 and ball 62 can be constructed in a variety of ways known to the prior art. Particularly, preferred constructions of these components are described in U.S. Pat. Nos. 3,820,167, 3,943,576, 3,996,625 and 4,077,070, which are hereby incorporated in their entireties by reference.

Femur portion 54 also includes collar 14. The collar 14 includes a body 64 having outer surfaces 66. The outer surfaces may be coated with a material, which provides for bony ingrowth. One such coating is marketed by DePuy Orthopaedics, Incorporated as Porocoat®. This coating is more fully described in U.S. Pat. No. 3,855,638 to Pilliar hereby incorporated in its entirety by reference.

The collar 14 also includes walled aperture 70 for receiving the stem 56. The walls of aperture 70 taper inwardly from the top to the bottom of the collar 14 and mate with a complimentary taper on the outside of stem 56. The slopes of these tapers are chosen so that the stem and collar lock together as the stem is pushed into the collar. To further secure stem 56 to collar 14, the stem is provided with pins 72, which are received in recesses or prosthesis orientation features 34, formed in the collar 14. The pins in recesses prevent rotation of the stem 56 within aperture 70.

Outer surface 66 of collar 14 is contoured to mate with inner surfaces 74 of the hard bone portion 76 of bone 12. That is, outer surface 66 is given a shape such that, when collar 14 is implanted in a suitably prepared bone, e.g., the upper part of the femur for the hip prosthesis, a substantial fraction of the hard bones inner surface 74 is in close proximity to or in contact with the prosthesis' outer surface 66.

Figure 2:
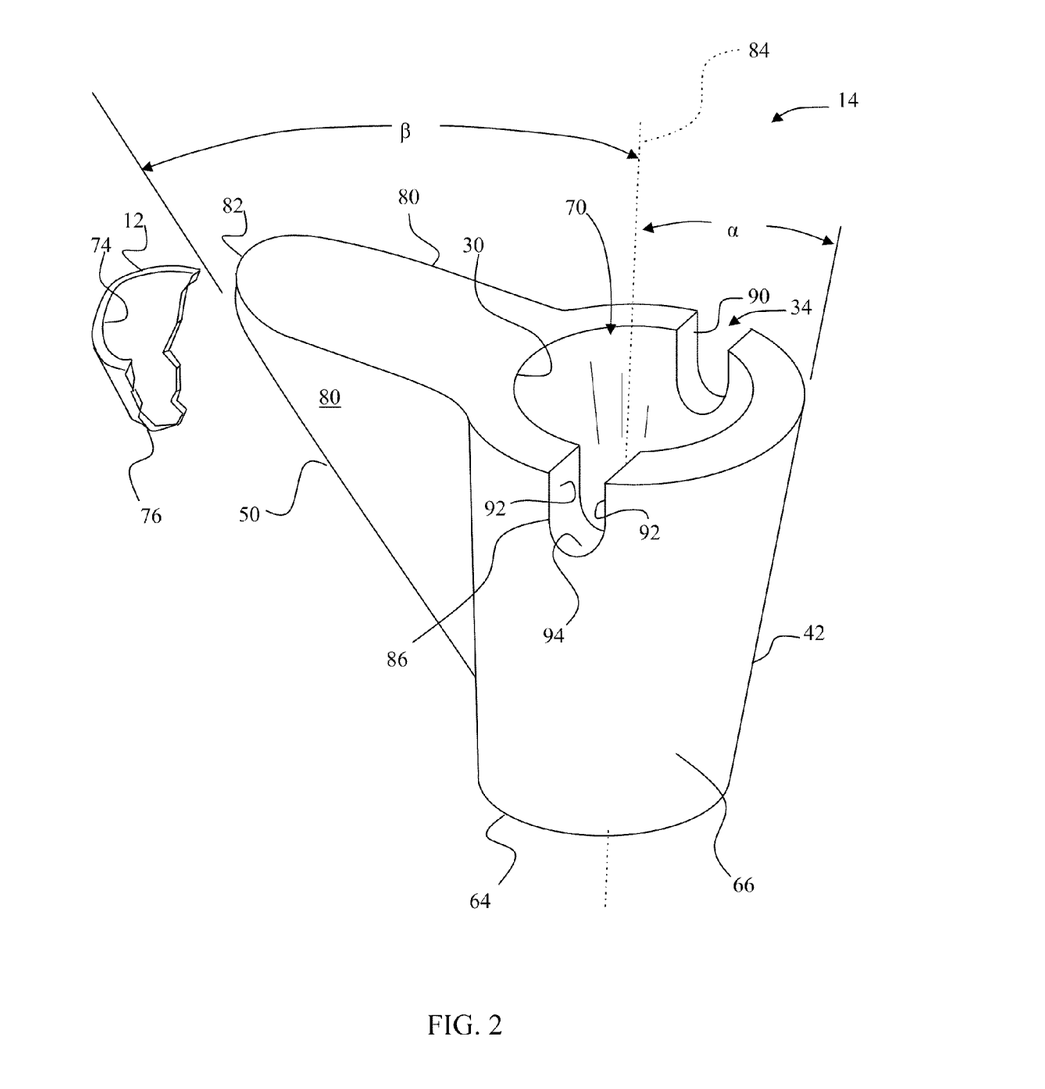
FIG. 2 is an enlarged perspective view of a femoral component of a hip prosthesis with which the kit of FIG. 1 may be used.

Referring now to FIG. 2, the collar or sleeve 14 is shown in greater detail. The sleeve 14 includes the body 64 with outer periphery 66, which closely conforms to inner surface 74 of the cortical bone 76 of the long bone 12.

The body 64, as shown in FIG. 2, includes a first portion 42 at which outer surface 66 has a generally conofrustrical shape. The second portion 50 of the prosthesis 14 has a shape, which is a generally wedge shaped having opposed generally parallel faces 80 connected to each other by curved portions 82. The conofrustrical first portion 42 may be defined by angle α extending from axis 84 to outer surface 66 of the first portion 42.

The wedge shaped second portion 50 of the prosthesis sleeve 14 may be defined by angle β from the sleeve centerline 84 to the curved portion 82 of the outer surface 66 of the second portion 50 of the prosthesis 14.

As shown in FIG. 2, the prosthesis orientation feature 34 may be in the form of opposed first recess 86 and second recess 90. The recesses 86 and 90 include opposed walls 92 and an arcuate portion 94.

Figure 3:
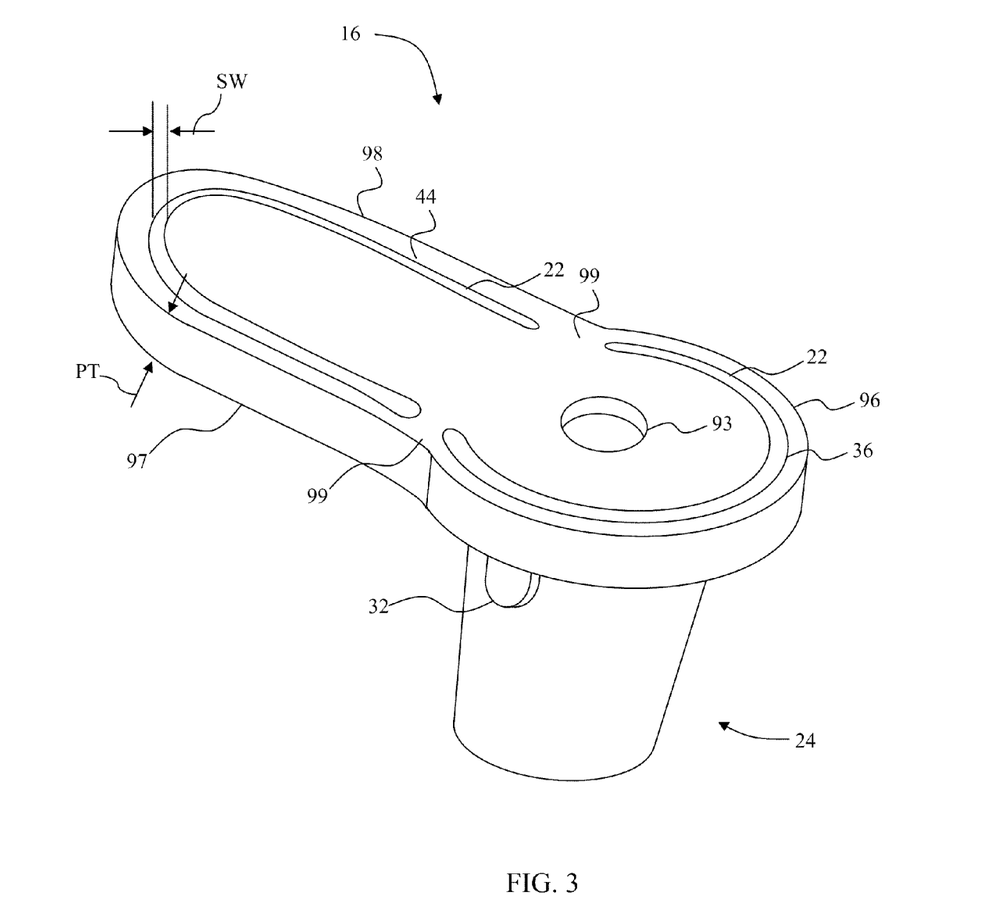
FIG. 3 is an enlarged perspective view of the guide of FIG. 1.

Referring now to FIG. 3, the guide 16 is shown in greater detail. The guide 16 includes the second portion 24 which mates and cooperates with internal taper 30 of the aperture 70 of the sleeve 14. The second portion 24 includes an external taper, which preferably mates with internal taper 30 of the sleeve 14. The second portion 24 preferably includes a guide orientation feature 32 in the form, for example, a protrusion which mates with stem alignment feature or recess 34. The guide orientation feature may have any suitable shape and may, for example, have an external periphery which closely conforms to the periphery of the recess 34.

The guide 16 may utilize a single channel, or, as shown in FIG. 3, a plurality of channels 22 may be used. For example, and as shown in FIG. 3, a first channel 36 may be positioned in first portion 96 of plate portion 97 of the guide 16. Further, a second channel 44 may be positioned in second portion 98 of the plate portion 97 of the guide 16.

The first portion 96 of the plate portion 97 of the guide 16 corresponds to the first portion 42 of the sleeve 14, and the second portion 98 of the plate portion 97 of the guide 16 corresponds to the second portion 50 of the sleeve 14.

The first channel 36 and the second channel 44 have a channel width SW, which is sized for rotating fit with the tool diameter TD of the tool 20. The slot width SW of the channels 36 and 44 are sized slightly larger than the tool diameter TD of the tool 20 so that tool 20 may provide an accurate cut of the bone 12.

The first channel 36 preferably forms an angle αα with prosthesis axis 84 (see FIG. 7) which angle αα is preferably the same as angle α of the outer surface 66 of the body 64 of the sleeve 14, so that a minimal amount of bone is removed by the guide 16. Similarly, the second channel 44 forms an angle ββ with the prosthesis centerline 84 and the angle 84 is preferably is the same as angle β of the outer surface 66 of the body 64 in the second portion 50 of the sleeve 14.

It should be appreciated that the angle β β and the angle β are not a constant angle, but vary depending on the portion of outer surface 66 of the sleeve 14. For example, β is different in the portion of the outer surface 66 of the sleeve than that of the faces 80 from that of β in the arcuate portions 82 of the second portion 50 of the sleeve 14. Preferably, however, the angles β and β β of the sleeve 14 and the guide 16 are equal at the corresponding positions along the sleeve 14 and the guide 16.

Continuing with FIG. 3, the plate portion 97 of the guide 16 has a thickness PT sufficient to provide for strength to control the location of the tool 20. The guide 16 is made of a suitable durable material, for example a metal, for example tool steel or any material that may be sterilized using commercially available sterilization equipment.

To provide for structural integrity of the plate portion 97, the first channel 36 and the second channel 44 are spaced from each other by, for example, lands 99. Also, optionally, the plate portion 97 of the guide 16 may include a construction and removal hole 93, which is preferably positioned concentric with prosthesis centerline 84 to provide for easy removal of the guide 16 after the cuts have been made by the tool 20.

Referring again to FIG. 3, the construction and removal hole 93 may include internal threads not shown which may be compatible with threads (not shown) in a slap hammer type device (not shown).

Figure 6:
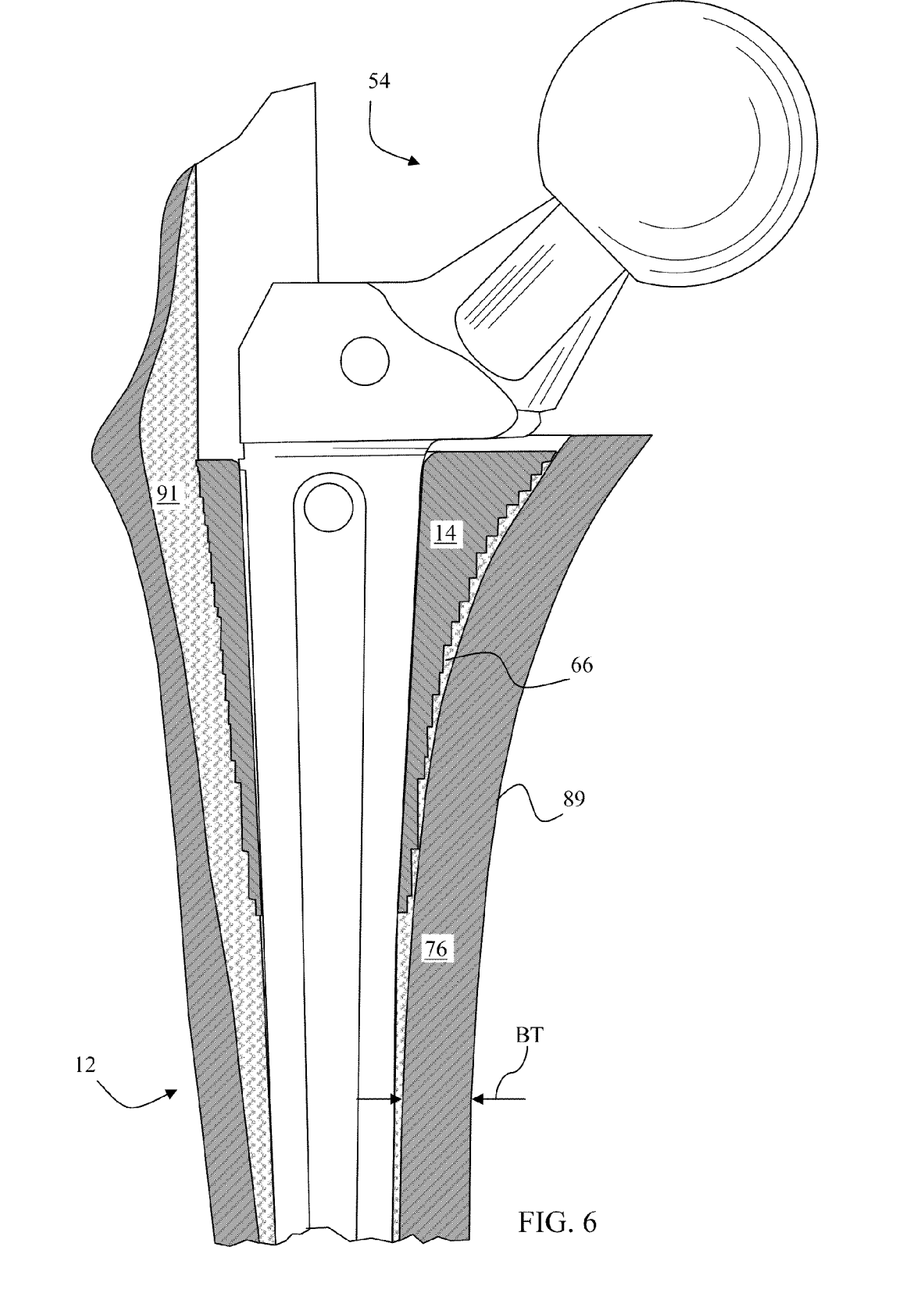
FIG. 6 is a plan view partially in cross section of the femoral hip stem prosthesis assembly of FIG. 5.

Referring now to FIG. 6, the hip stem 54 is shown with the sleeve 14 installed and the hip stem positioned in long bone 12. As can be shown by FIG. 6, the hip stem 54, when installed, may result in the removal of a large portion cancellous bone 91 within the long bone 12. A portion of the cancellous bone 91 may still remain.

It should be appreciated that the tool must remove bone from between outer surface 66 of the sleeve 14 and outer periphery 89 of the cortical bone 76 of the long bone 12. As bone thickness BT between the outer surface 66 of the sleeve 14 and outer periphery 89 of the cortical bone 76 becomes smaller, the corresponding tool required to remove the prosthesis should be smaller.

Figure 7:
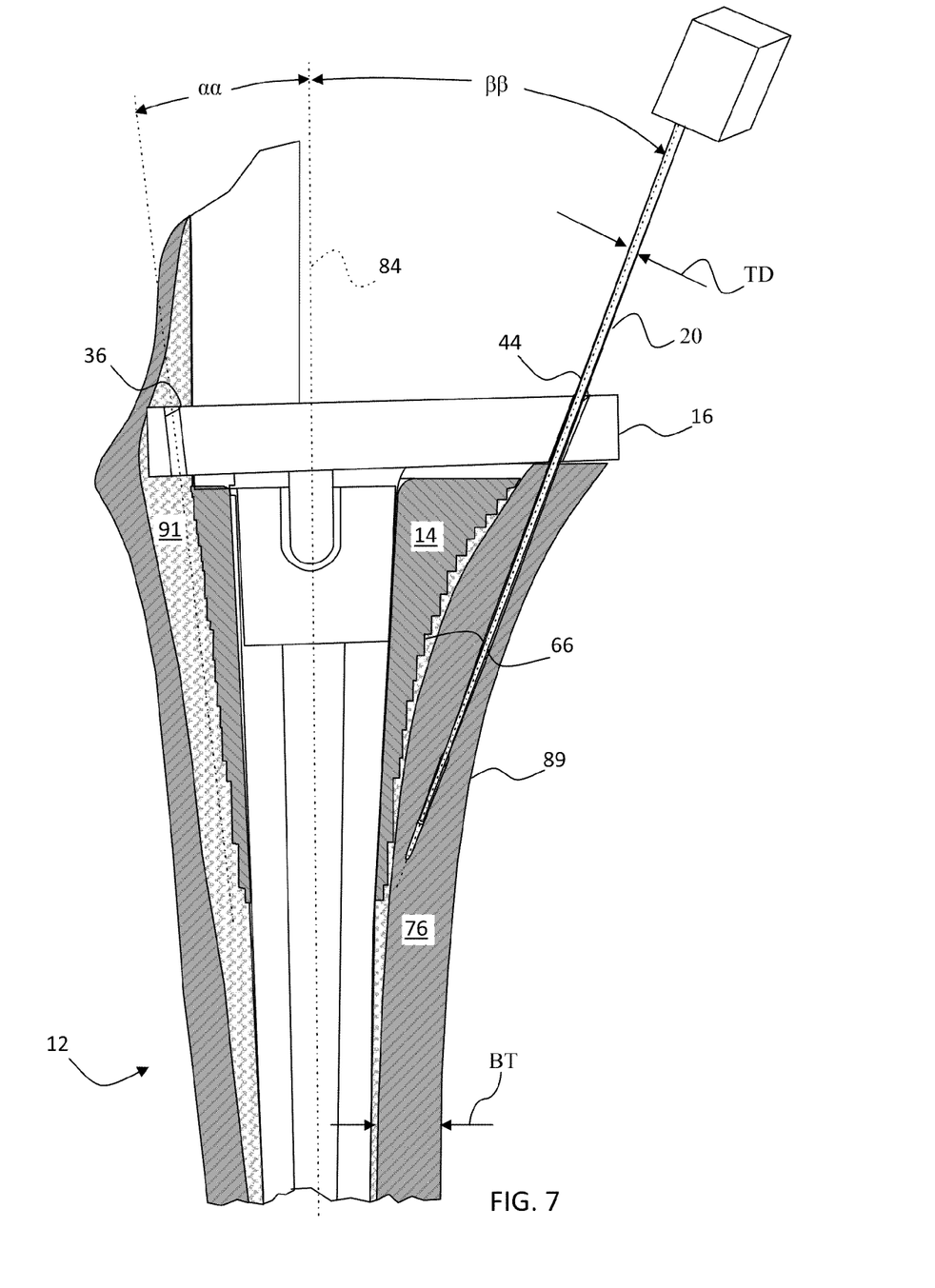
FIG. 7 is a plan view, partially in cross section, of the femoral hip stem prosthesis assembly of FIG. 6 installed in a femur with the stem removed the guide of FIG. 3 installed.

Referring now to FIG. 7, the guide 16 is shown positioned on sleeve 14 with the sleeve 14 in position in long bone 12. As can be seen in FIG. 7, the tool 20 has a tool diameter TD to provide for a portion of the long bone 12 to remain after the removal of the sleeve 14 requires that the tool diameter TD be considerably less than the bone thickness BT between the sleeve 14 and the cortical bone 76. In fact, because of the arcuate nature of the long bone, particularly adjacent, second portion 50 of the prosthesis sleeve 14 the tool diameter TD must be considerably smaller than the bone thickness BT. For example, and as shown in FIG. 7, the second channel 44 of the guide 16 forms an angle β β with the centerline 84 of the sleeve 14 such that the tool 20 is very closely spaced from both the distal and proximal ends of the sleeve 14 to minimize the removal of bone from the long bone 12.

Referring again to FIG. 7, it should be appreciated that to accommodate different sizes of the patient and the correspondingly different sizes of the long bone 12, the sleeve 14 may be available in a variety of sizes. For each particular size of sleeve 14, a particular sized guide 16, preferably, is uniquely designed to be compatible with that particular sleeve. Correspondingly, the channels for the guide will be correspondingly designed to closely conform with the outer periphery of the particularly sized sleeve. Such series of guides 16 will provide for a minimal bone removal regardless of the size of the sleeve.

Figure 4:
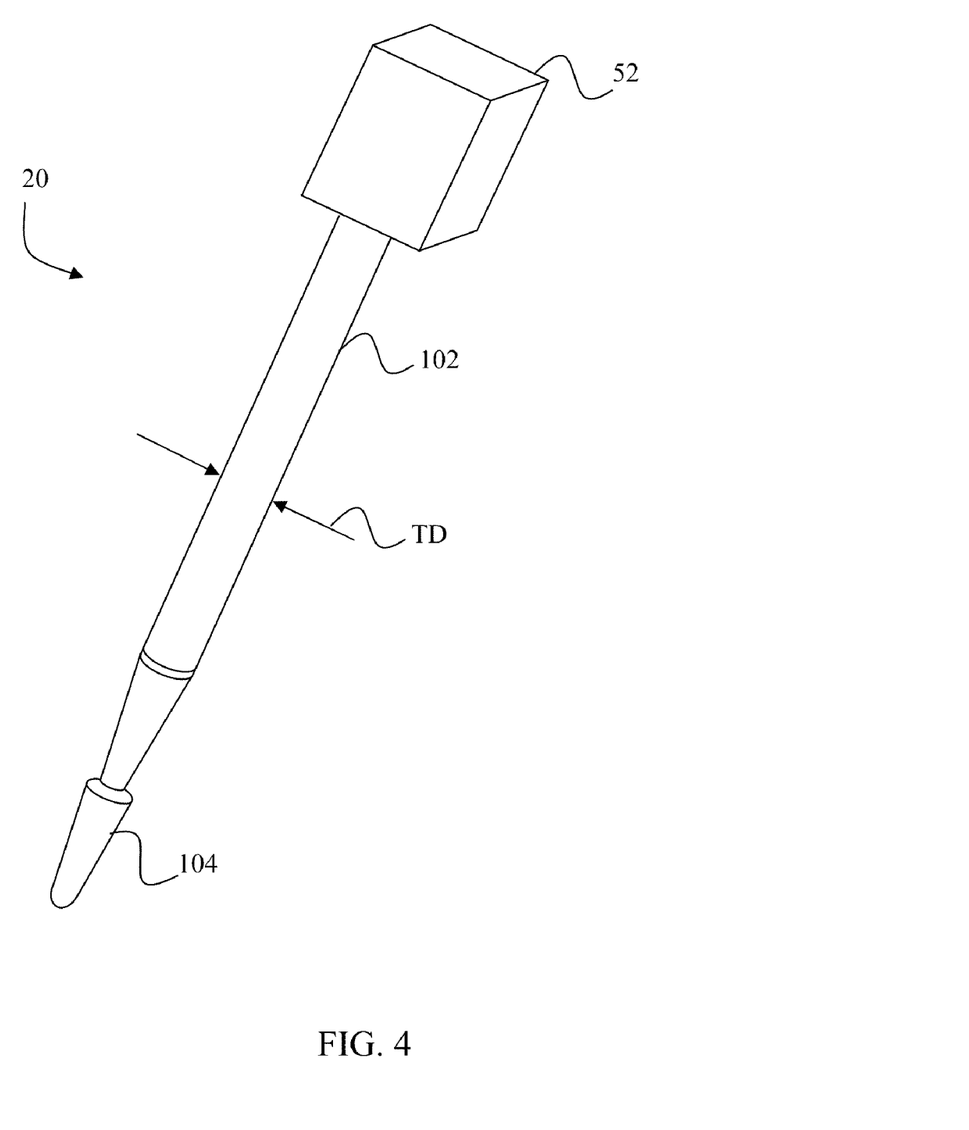
FIG. 4 is an enlarged perspective view of the tool of FIG. 1.

Referring now to FIG. 4, the tool 20 is shown in greater detail. The tool 20 may have any suitable size and shape; but preferably, as previously mentioned, the tool 20 preferably has a thickness or diameter as small as practically possible to minimize the bone removed. The tool 20 includes a shank 102 as well as a cutting surface 104 extending from an end of the shank 102.

The tool 20 may any suitable shape and may, as shown in FIG. 4, have a general elongated cylindrical shape and may be designed for rotational operation or, it should be appreciated that the tool 20 may be adapted for oscillating operation and may be in the form of a generally planer blade.

The tool 20 may be made of any suitable, durable material and may, for example, be made of a metal, for example an alloy steel, for example tool steel. The cutting surface 104 may be integral with the shank 102 or be made of a separate component, and for example, a different material, such as carbide.

It should be appreciated that the tool 20 should be made of a material that is sterilizable, for example, a metal.

The tool 20 may be caused to move by the manual operation by the surgeon or may, as shown in FIG. 4, be connected to a power source 52, for example, a rotational power source which may be either electrical, pneumatic, or hydraulic. Preferably, the power source 52 is suitable for use in an operating room. Such power sources are readily available.

Figure 8:
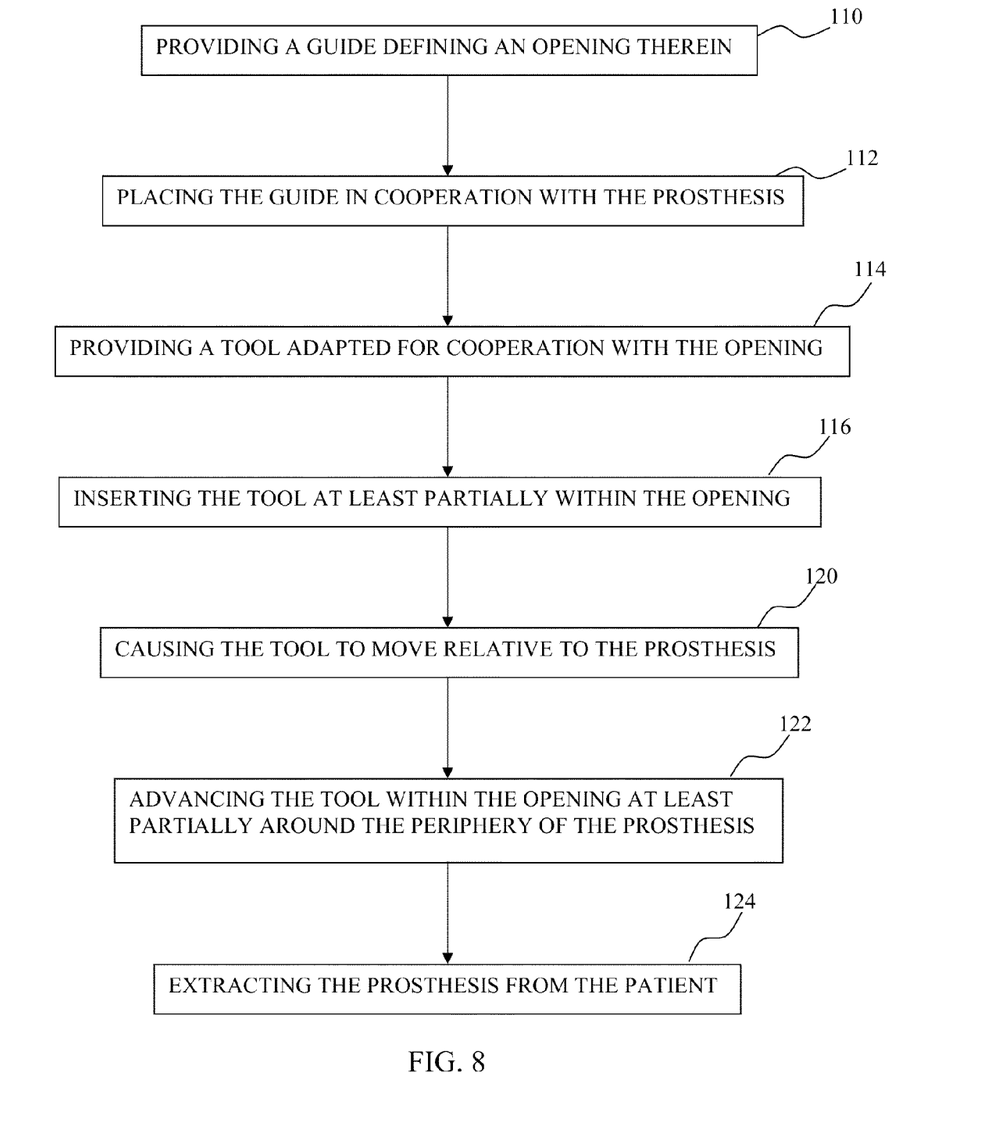
FIG. 8 is a process flow chart for a method of removing an implanted prosthesis according to an embodiment of the present invention.

Referring now to FIG. 8, a method for removing a prosthesis is shown. The method includes a first step 110 of providing a guide defining an opening in the guide. The method further includes a second step 112 of placing the guide in cooperation with the prosthesis. The method includes a third step 114 of providing a tool adapted for cooperation with the opening. The method also includes a fourth step 116 of inserting the tool at least partially within the opening.

Further, the method includes a fifth step 120 of causing the tool to move relative to the prosthesis. The method also includes a sixth step 122 of advancing the tool within the opening at least partially around the periphery of the prosthesis, and a seventh step 124 of extracting the prosthesis from the patient.

Although the present invention and its advantages have been described in detail, it should be understood that various changes, substitutions, and alterations can be made therein without departing from the spirit and scope of the present invention, as defined by the appended claims.

What is claimed:

1. A method of removing an implanted prosthesis comprising:
    incising a patient to expose a prosthesis implanted in a bone of the patient;
    attaching a guide to the exposed prosthesis, the guide including a coupling portion and a guide portion, the guide portion including a first bone facing surface that defines a first slot, the attachment of the guide to the exposed prosthesis including attaching the coupling portion of the guide to the prosthesis such that the first bone facing surface of the guide portion of the guide faces a first surface portion of the bone adjacent to the prosthesis with the first slot spaced from an outer surface of the prosthesis;
    moving a cutting tool into the first slot in the guide portion of the guide;
    moving a cutting portion of the cutting tool through the first bone facing surface from the first slot;
    contacting the first surface portion of the bone adjacent to the prosthesis with the cutting portion at a location in the first surface portion spaced from the outer surface of the prosthesis;
    removing a portion of the bone adjacent to the prosthesis by moving the cutting portion through the bone at least partially about the periphery of the prosthesis spaced from the outer surface of the prosthesis; and
    removing the prosthesis from the bone.

2. The method of claim 1, further comprising:
    mating a protuberance on the coupling portion of the guide with an orientation feature on the prosthesis prior to contacting the first surface portion of the bone.

3. The method of claim 1, wherein contacting the first surface portion of the bone comprises:
    plunging a tip portion of the cutting portion into the bone.

4. The method of claim 3, further comprising:
    contacting the bone with a side cutting portion of the cutting portion by moving the cutting tool along the first slot.

5. The method of claim 4, wherein contacting the bone with a side cutting portion of the cutting tool comprises:
    moving the cutting tool in an arcuate path along the first slot.

6. The method of claim 1, further comprising:
    withdrawing the cutting portion through the first slot;
    moving the cutting portion into a second slot defined by a second bone facing surface in the guide portion of the guide generally opposite the first bone facing surface, wherein the second slot is not contiguous with the first slot;
    moving the cutting portion through the second bone facing surface from the second slot; and
    contacting a second surface portion of the bone adjacent to the prosthesis with the cutting portion by moving the cutting portion through the second bone facing surface from the second slot.

7. The method of claim 6, wherein contacting the second surface portion of the bone adjacent to the prosthesis with the cutting portion by moving the cutting portion through the second bone facing surface from the second slot comprises:
   contacting the second surface portion of the bone adjacent to the prosthesis with the cutting portion at an angle with respect to a longitudinal axis of the prosthesis different than the angle with respect to the longitudinal axis of the prosthesis at which the first surface portion of the bone adjacent to the prosthesis was contacted by moving the cutting portion through the first bone facing surface of the guide from the first slot.

8. The method of claim 1, wherein contacting the first surface portion of the bone adjacent to the prosthesis with the cutting portion by moving the cutting portion through the first bone facing surface from the first slot comprises:
   rotatably contacting the first surface portion of the bone adjacent to the prosthesis.

9. The method of claim 1, wherein removing a portion of the bone adjacent to the prosthesis comprises:
   creating a gap between the portion of the bone adjacent the prosthesis and an outer periphery of a cortical bone portion of the bone.

10. The method of claim 1, wherein removing a portion of the bone comprises:
   removing a portion of the bone adjacent to the prosthesis by moving the cutting portion along the first slot in a pattern which corresponds to the outer periphery of the prosthesis.

11. The method of claim 1, wherein the prosthesis includes a cavity which defines an internal surface, and wherein attaching the guide portion of the guide to the prosthesis includes:
   positioning the coupling portion of the guide in contact with the internal surface.

* * * * *